(12) United States Patent
Lips et al.

(10) Patent No.: US 8,565,857 B2
(45) Date of Patent: Oct. 22, 2013

(54) CATHETER AND MEDICAL ASSEMBLY

(75) Inventors: Oliver Lips, Hamburg (DE); Bernd David, Huettblek (DE); Bernhard Gleich, Hamburg (DE); Sascha Krueger, Hamburg (DE); Steffen Weiss, Hamburg (DE); Daniel Wirtz, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1072 days.

(21) Appl. No.: 12/440,252

(22) PCT Filed: Sep. 7, 2007

(86) PCT No.: PCT/IB2007/053611
§ 371 (c)(1),
(2), (4) Date: Mar. 6, 2009

(87) PCT Pub. No.: WO2008/032249
PCT Pub. Date: Mar. 20, 2008

(65) Prior Publication Data
US 2010/0041977 A1 Feb. 18, 2010

(30) Foreign Application Priority Data
Sep. 11, 2006 (EP) .................................. 06120423

(51) Int. Cl.
*A61B 5/05* (2006.01)
(52) U.S. Cl.
USPC ........... 600/424; 600/374; 600/407; 600/547; 600/595

(58) Field of Classification Search
USPC ........................ 600/424, 374, 407, 547, 595
See application file for complete search history.

(56) References Cited

U.S. PATENT DOCUMENTS

| | | | |
|---|---|---|---|
| 4,951,672 A * | 8/1990 | Buchwald et al. | 600/421 |
| 6,032,063 A * | 2/2000 | Hoar et al. | 600/372 |
| 6,741,882 B2 | 5/2004 | Schaffter et al. | |
| 7,039,455 B1 | 5/2006 | Brosovich et al. | |
| 2004/0263172 A1 | 12/2004 | Gray et al. | |
| 2005/0124898 A1 | 6/2005 | Borovsky et al. | |
| 2006/0030774 A1 | 2/2006 | Gray et al. | |
| 2007/0197891 A1* | 8/2007 | Shachar et al. | 600/374 |

FOREIGN PATENT DOCUMENTS

| | | |
|---|---|---|
| EP | 1488738 A1 | 12/2004 |
| WO | 9725761 A1 | 7/1997 |
| WO | 2005053555 A1 | 6/2005 |
| WO | 2006015938 A1 | 2/2006 |

* cited by examiner

*Primary Examiner* — Joel Lamprecht

(57) ABSTRACT

The present invention relates to a catheter (6) comprising: a connector (65, 66) at a proximal side of the catheter for connecting the catheter to an external signal transmission/receiving unit (10) for transmitting and/or receiving signals, an electrode (63, 64) at a distal side of the catheter, and an electrical connection including an electrical wire (61, 62) for electrically connecting the electrode and the connector for the transmission of signals between the electrode and the connector, wherein the electrical connection has a high electrical resistance of at least 1 kΩ, in particular of at least 5 kΩ. Thus, the present invention provides a solution to prevent excessive heating during EP interventions under MR guidance by using highly resistive wires and or lumped resistors as connections within catheters.

12 Claims, 2 Drawing Sheets

CATHETER AND MEDICAL ASSEMBLY

FIELD OF THE INVENTION

The present invention relates to a catheter comprising:
a connector at a proximal side of the catheter for connecting the catheter to an external signal transmission/receiving unit for transmitting and/or receiving signals,
an electrode at a distal side of the catheter, and
an electrical connection including an electrical wire for electrically connecting the electrode and the connector for the transmission of signals between the electrode and the connector.

Further, the present invention relates to a medical assembly comprising such a catheter.

BACKGROUND OF THE INVENTION

So far electrophysiologic (EP) interventions cannot be performed safely under magnetic resonance (MR) guidance due to the risk of radio frequency (RF) heating. For EP procedures it is necessary to monitor the intracardiac electrocardiogram (IECG) ("mapping") and/or to stimulate the heart ("pacing"). Both require an electrical connection to electrodes on the catheter tip, which is placed inside the heart. This connection can become resonant at the operating frequency of the MR scanner and thus act as an antenna for the applied RF fields, leading to excessive heating especially at the tips.

The wires, which are connected between the electrodes at the catheter tip ("distal side") and the connections at the other side ("proximal side") of the catheter, become resonant if they fulfill the condition $$l \approx n\frac{\lambda}{2} = n\frac{\lambda_0}{2\sqrt{\varepsilon_r \mu_r}},$$

with $\lambda_0$ denoting the wavelength in vacuum, $l$ the length of the wire, $\varepsilon_r$ and $\mu_r$ the effective relative permittivity and permeability for the common mode. The effective $\varepsilon_r$ and $\mu_r$ depend strongly on the properties of the tissue surrounding the wire. As a consequence it is hardly possible to predict if resonance will occur during an intervention, since the length of wire inside the patient as well as the surrounding of the wire changes continuously. This means that EP catheters have to be made inherently RF-safe.

WO 2005/053555 A1 discloses an electrode catheter for the defibrillation, mapping or ablation of cardiac tissue. Said catheter comprises a terminal on the proximal end of the electrode catheter and one or more sensing and/or treatment electrodes that are situated on or in the vicinity of the distal end of the electrode catheter, in addition to at least one electric conductor, which is used to electrically connect a respective sensing or treatment electrode to the terminal. The electric conductor is composed of carbon and the electrode catheter is configured to be suitable for use as part of magnetic resonance tomography and for connection to electrophysiotherapy equipment. Said catheter comprises at least one defibrillation electrode, or at least one sensing electrode for the recording and evaluation of cardiac tissue potentials, or at least one treatment electrode for delivering high-frequency currents for ablation purposes. However, said carbon is not sufficiently RF-safe for medical applications in the field of MR.

SUMMARY OF THE INVENTION

It is an object of the present invention to provide a catheter and a medical assembly using such a catheter which can be used during medical interventions under MR guidance without the risk that the electrical connection of the catheter becomes excessively hot due to resonance at the operating frequency of the MR scanner.

In a first aspect of the present invention a catheter as described above is presented that is characterized in that the electrical connection has a high electrical resistance of at least 1 k$\Omega$, in particular of at least 5 k$\Omega$.

In a further aspect of the present invention a medical assembly is presented comprising:
characterized in that the electrical connection has a high electrical resistance of at least 1 k$\Omega$, in particular of at least 5 k$\Omega$,
a signal transmission/receiving unit for transmitting signals to and/or receiving signals from the electrode of said catheter and for processing said signals.

Preferred embodiments of the invention are defined in the dependent claims.

The present invention is based on the idea to use a highly resistive electrical connection for the transmission of signals between the external equipment (e.g. the pacing unit or the ECG unit) and the catheter tip. A high resistance limits the induced current in the wires and thus effectively attenuates heating. Despite the high resistance the signal quality is sufficient.

According to a preferred embodiment of the present invention the usage of highly resistive wire(s) in the catheter for connecting the electrodes at the tip to the connector at the other side for connection to an external equipment (generally called signal transmission/receiving unit) is proposed. The wire can have an electrical resistance of at least 1 k$\Omega$/m, in particular of at least 5 k$\Omega$/m.

An alternative (or additional) solution is to insert one or more current limiting resistors into the connection to reduce the RF-heating. The resistor(s) can have a resistance of at least 1 k$\Omega$, in particular of at least 5 k$\Omega$.

The invention can be used for mapping as well as pacing, although in the latter case additional measures may need to be applied to reduce the risk for injuries caused by the high voltages required for the stimulation system. When used for mapping, the wires of the highly resistive connection are used to carry the signals (in particular ECG signals) picked up by the electrodes to the external equipment. When used for pacing, the wires of the highly resistive connection are used to carry the pacing signals applied by the external equipment to the connector to the electrodes at the catheter tip.

Preferably, the electrical connection comprises a pair of wires for electrically connecting a pair of electrodes with the connector. Often, a catheter comprises a plurality of electrodes from which 2 electrodes are used for a heart stimulation (bipolar). Generally, also one electrode of the catheter is sufficient, where an external reference electrode is used in addition (unipolar).

To avoid any risk that too high currents or voltages my cause any damage to a patient's health during an intervention, a preferred embodiment of the catheter comprises a current sensing unit for sensing the electrical current flowing in the electrical connection at the distal side of the catheter and for transmitting a sensing signal indicative of the sensed current to an external current control unit. Thus, a current leakage between the catheter input and the catheter tip can be recognized, and countermeasures can be taken by the current control unit, e.g. the current flowing in the wire(s) of the electrical connection can be reduced or stopped.

In an advantageous embodiment, that is easy to implement, the current sensing unit comprises a sensing resistor having a small electrical resistance of 1 k$\Omega$ for sensing a voltage representing said sensing signal and a pair of sensing wires for transmitting said sensing signal to said external current control unit.

Preferred embodiments of the materials that can be used for said wire(s) are defined in further dependent claims enabling a practical handling, which would not be possible with a very thin Cu wire.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
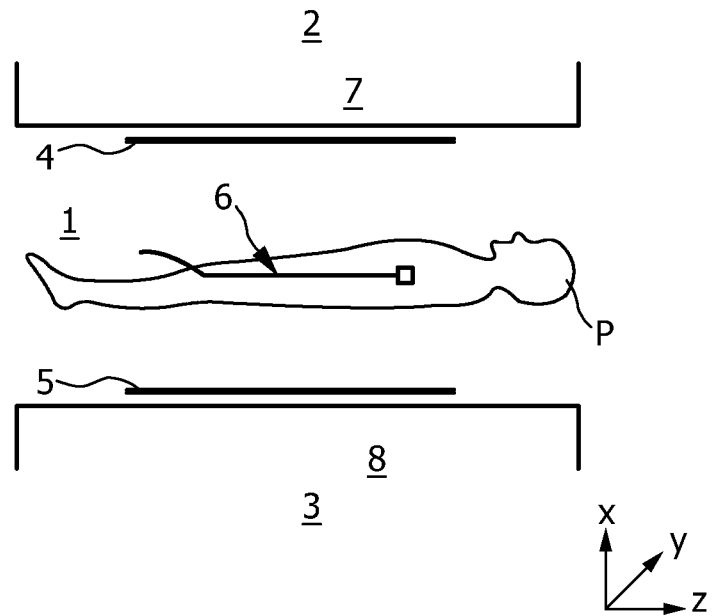
FIG. 1 shows a diagrammatic side elevation of an MR imaging apparatus.

FIG. 1 exemplarily shows components of an open MR imaging apparatus which are of essential importance for the generation and reception of magnetic fields in an examination zone 1. Above and underneath the examination zone 1 there are provided respective magnet systems 2, 3 which generate an essentially uniform main magnetic field (B0 field for magnetizing the object to be examined, that is, for aligning the nuclear spins) whose magnetic flux density (magnetic induction) may be in the order of magnitude of between some tenths of Tesla to some Tesla. The main magnetic field essentially extends through a patient P in a direction perpendicular to the longitudinal axis of the patient (that is, in the x direction).

Planar or at least approximately planar RF conductor structures (resonators) in the form of RF transmission coils 4 ("body coils") are provided for generating RF pulses (B1 field) of the MR frequency whereby the nuclear spins are excited in the tissue to be examined, said RF transmission coils 4 being arranged on the respective magnet systems 2 and/or 3. RF receiving coils 5 are provided for receiving subsequent relaxation events in the tissue; these coils 5 may also be formed by RF conductor structures (resonators) provided on at least one of the magnet systems 2, 3. Alternatively, one common RF resonator can also be used for transmission and reception if it is suitably switched over, or the two RF resonators 4, 5 can serve for the alternating transmission and reception in common.

Furthermore, for the spatial discrimination and resolution of the relaxation signals emanating from the tissue of a patient P (localization of the excited states) there are also provided a plurality of gradient magnetic field coils 7, 8 whereby three gradient magnetic fields are generated which extend in the direction of the x axis. Accordingly, a first gradient magnetic field varies essentially linearly in the direction of the x axis, while a second gradient magnetic field varies essentially linearly in the direction of the y axis, and a third gradient magnetic field varies essentially linearly in the direction of the z axis.

In order to monitor the intracardiac electrocardiogram (IECG) ("mapping") and/or to stimulate the heart ("pacing") of the patient P, use is often made of a catheter 6 which is introduced into the patient P to provide an electrical connection to electrodes on the catheter tip. So far electrophysiologic (EP) interventions, however, cannot be performed safely under MR guidance due to the risk of RF heating of the electrical connection, which can become resonant at the operating frequency of the MR scanner and thus act as an antenna for the applied RF fields, leading to excessive heating.

Figure 2:
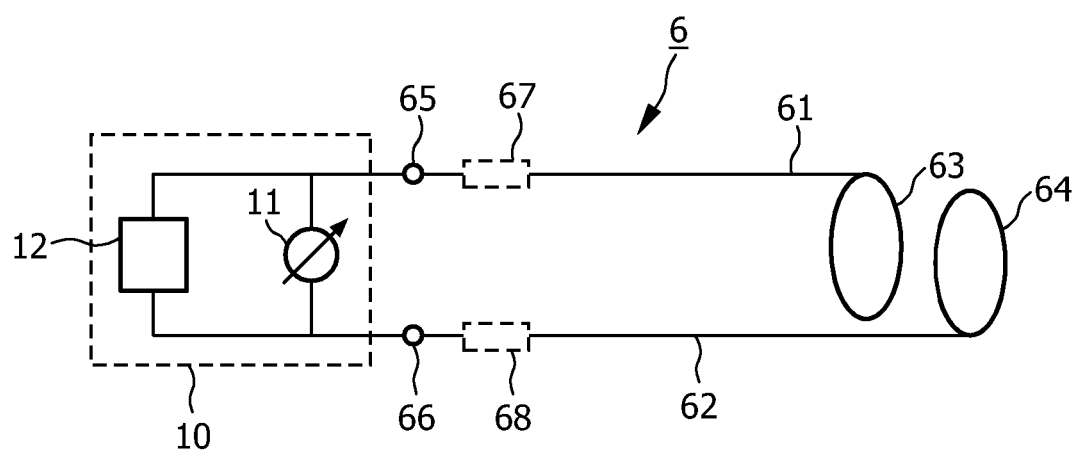
FIG. 2 shows a first embodiment of the medical assembly according to the present invention.

FIG. 2 shows a first embodiment of the medical assembly including a catheter 6 according to the present invention. The catheter in this embodiment comprises two wires 61, 62 for connecting a pair of electrodes 63, 64 at the tip of the catheter 6 to an external equipment 10 (signal transmission/receiving unit) connected to connection terminals 65, 66 (the connector) for the transmission of signals therebetween. In the shown embodiment the external equipment 10 comprises an ECG monitoring unit 11 for receiving and processing of ECG signal received by the electrodes 63, 64 and a EP stimulating unit 12 for generating and transmitting of pacing signals for stimulating the heart of the patient P. It is evident that these are just shown as examples and that the external equipment 10 does neither require both these units 11, 12 nor is it limited to these units 11, 12.

According to the present invention highly resistive wires 61, 62 and/or wires with additional lumped resistors 67, 68 are used as connections within the catheter 6. A high resistance limits the induced current in the leads and thus effectively attenuates resonance effects. In this context it has to be mentioned, that the heating of the conductor 6 itself generally does not pose the safety problem (as often incorrectly stated). Instead the electric fields E near the conductors 61, 62 lead to a power deposition in the tissue, which is described by the specific absorption rate $$SAR = \frac{\sigma E^2}{2\rho},$$

with σ and ρ respectively being the conductivity the mass density of the tissue. Reducing the current inside the conductor 6 leads to lower electric fields at its tip, since both are related.

The current can principally be reduced by lumped resistors 67, 68, but they have to be placed at positions, where the highest currents occur, i.e. in the antinodes of the induced standing wave. If they are put into the nodes of the standing wave, they are not effective. The problem of proper a-priori placement does not occur when using highly resistive wires 61, 62, where the resistance is distributed. Furthermore, in contrast to lumped elements highly resistive wires do not introduce additional joints. Nevertheless, it is principally possible to insert (preferably additional) lumped resistors 67, 68 into the highly resistive wires 61, 62 to increase the resistance further or to use low resistance cables with lumped resistors placed at distances much smaller than λ/2.

Figure 3:
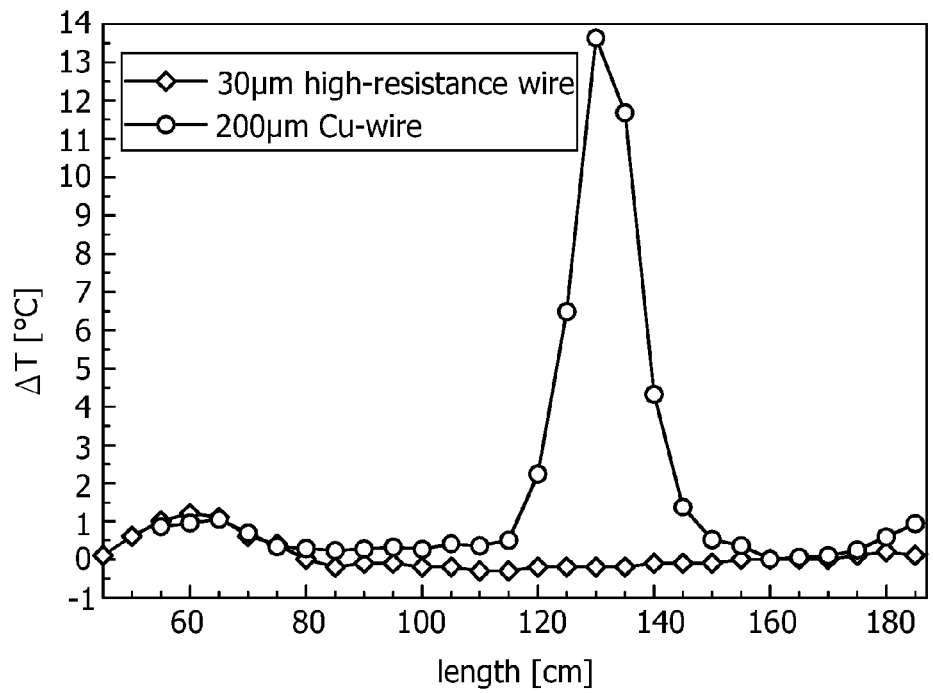
FIG. 3 shows a diagram illustrating the temperature change for two different wires used in a catheter.

Test measurements performed on a highly conductive copper wire and a resistive wire of 1.8 kΩ/m (metallic alloy ISAOHM, Isabellenhütte) being put into a catheter surrounded by a phantom liquid mimicking the human body demonstrate the advantage of the invention. The wires were in contact with the phantom fluid at the tip of the catheter as in a real EP catheter. The length of the catheter was varied to achieve the resonance condition. The temperature increase at the tip was measured during an MR scan. The results presented in FIG. 3 show, that for a copper wire a pronounced resonance effect occurs leading to excessive heating, whereas the resistive wire does not cause clinically significant heating.

Besides the safety aspect there is the requirement that the wire is adequate to transmit signals or stimulating pulses, respectively. Typical ECG recorders 11 have input impedances of several hundred MΩ up to GΩ, which means that the voltage drop of the cable is negligible, even if the cable resistance reaches several MΩ. Also the thermal noise of such a line is much lower than typical ECG voltages.

The situation may need further attention in the case of pacing or any other method, which has to bring a voltage/current to the catheter tip. Since the resistance between the tip electrodes 63, 64 (typically about 100Ω) is much smaller than that of the highly resistive wire, most of the power is lost in the cable. As a consequence high voltages have to be applied to achieve the required currents/voltages at the catheter tip. As an example for a pacing current of 2 mA between the electrodes and a 100 kΩ resistance of the connecting cables 200 V must be applied. This poses safety considerations, since inside the body already low voltages can cause dangerous shocks.

Figure 4:
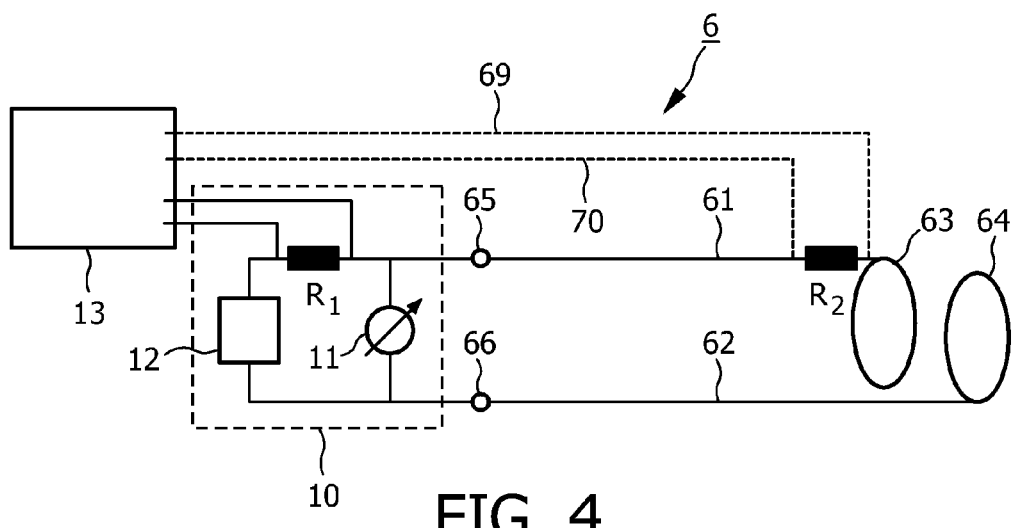
FIG. 4 shows a further embodiment of the medical assembly according to the present invention.

This invention therefore provides additional, optional measures to provide adequate safety. An embodiment of a medical assembly using such additional safety measures is shown in FIG. 4.

A first such measure is to use a current limited power supply 13, so that even in the case of a short circuit no currents higher than the specified ones can flow through the wires 61, 62.

A second such measure is to avoid that e.g. in case of a breakdown of the cable insulation, a voltage is applied somewhere else than at the desired location. To this end, it is verified that the whole current, which is fed into the catheter 6, in fact reaches the tip. This may be realized by sensing the voltage drop of a resistor R2 at the tip of the catheter 6, which directly yields the corresponding current. This value is then compared with the current applied by the power source 13, which can e.g. be measured in the same way. For sensing the current at the tip, resistive wires 69, 70 are used that have a higher resistance than the resistance of the wires 61, 62 connecting the electrodes to the external equipment 10.

In this embodiment, the potential difference at the resistor R2 is monitored by the two wires 69, 70. The current at the tip is compared to the current fed into the catheter measured at the resistor R1 to detect a malfunction. Thus, the high voltage, which is necessary to achieve sufficiently high stimulation currents, does not pose a danger. It is not necessary to use lumped resistors R1, R2, but instead it is also possible to use small parts of the highly resistive wires 61, 62 to measure the potential differences.

Thus, the present invention provides the following features that can be used each on its own or in any one combination of features:
using highly resistive wires (and/or lumped resistors) inside catheters to monitor physiological signals (IECG) without danger of RF-heating (RF-safe);
using the same assembly to stimulate the heart (pacing);
using highly resistive wires (or cables with lumped resistors) to sense the current at the catheter tip for providing feedback information, e.g. for detecting malfunction or regulation purposes;
using highly resistive wires (or cables with lumped resistors) to sense non-physiological signals without RF-heating;
Using highly resistive wires an EP catheter can be built in the usual way, i.e. connecting the tip electrodes to the monitoring and pacing equipment. Optionally, additional filters may be inserted to remove MR-induced artifacts from the IECG signal.

Wires with resistances starting at roughly 1 kΩ/m are used to achieve RF-safety. As shown in FIG. 3 already resistances of 1.8 kΩ/m can reduce the heating substantially, but to avoid any risks higher values seem favourable for practical applications. Nevertheless, a compromise between safety (demanding high resistance) and applied power (demanding low resistance) has to be found. The wires can be made of metallic alloys (as in the example shown above: ISAOHM wire), carbon fibres, conductive polymers or any other non-magnetic material. A possible technique is to coat nonconductive fibres or threads with the conductive polymers. Also the catheter itself may be coated with such a conductive film. An alternative is to use nonconductive fibres or threads coated with very thin metallic surfaces (e.g. by sputtering). A further alternative is to use nonconductive fibres or threads filled (above the percolation threshold) with conductive particles. If necessary the resistance of the wires can be further increased adding lumped resistors.

The wires of the catheter according to the invention are of a high electrical resistance. This resistance is high in comparison to the traditionally used metal wires. The electrical resistance is that high that it sufficiently attenuates the current induced in the wire by the MR field. On the one hand, the electrical resistance of the connecting wires is preferably low in order not to degrade the signal and signal quality sensed by the electrodes. On the other hand, the electrical resistance is preferably high in order to attenuate the induced current. Thus, the value of the electrical resistance of the wires according to the invention is to be chosen such that both criteria (low enough for signal quality and high enough for attenuating MR induced current) are met. These suitable values form a range of electrical resistance values, with a lower boundary and an upper boundary. The lower boundary is such that the MR induced values are still sufficiently attenuated. The upper boundary is such that the signal quality is still sufficient to perform reliable measurements.

The exact values of the resistance of the wire depend, for example, on the position of such a wire inside the patient and inside the MR-scanner. Moreover the wire thickness, strength of excitation, number of wires inside one catheter play a role.

For the lower boundary of the range of values of electrical resistance of the wire, the following can be said. Experiments have shown that under bad conditions of having the wire very close to the wall of the MR-scanner the resistance of the wire must be larger that 2 kΩ/m (for a 30 μm thick wire) to suppress induced current sufficiently. In more favorable conditions it appeared that a resistance as low as 1 kΩ/m still provided for sufficient attenuation of the induced current. Preferably, values are higher than 5 kΩ/m. A preferred value lies between 5 and 20 kΩ/m.

For the upper boundary of the range of values of the electrical resistance of the wire, the following can be said. When the wire is used for mapping of ECG signals, i.e. measuring signals at the electrode, values up to 2 MΩ still provide good signal quality. When the wire is used for pacing, lower values of the electrical resistance must be used since electrical power will have to be transferred through the wire. This makes that the values is preferable less then 50 kΩ.

The above numbers are examples of the value of the electrical resistance according to the invention. It is to be noted, that in other circumstances other values could be preferable.

The invention can advantageously be used for EP interventions under MR guidance, allowing to record IECGs and to stimulate the heart. The concept of monitoring the voltage of a sensor in the catheter (in this case a current sensing resistor) may also be used for other applications. Generally the invention can be applied to all medical diagnosis and therapy involving the measurement of electrical signals or the application of electrical stimulation. With continuously increasing field strengths of MR systems, in future, even comparatively short leads of e.g. implantable devices may benefit from the proposed invention.

In summary, the present invention provides a solution to prevent excessive heating during EP interventions under MR guidance by using highly resistive wires and or lumped resistors as connections within catheters. A high resistance limits the induced current in the leads and thus effectively attenuates heating. The signal quality of the recorded IECG is preserved even if the cable resistance reaches several MΩ.

Thus, according to the present invention, with highly resistive wires the IECG can be measured safely without danger of RF-heating. The same type of cables can be used for cardiac pacing. The wires can be realized with a very low diameter. The safety concept is not limited to EP applications. It can be used to sense the output voltage of a pressure or temperature sensor. The optional current limitation and the current leakage detection protect the patient even in case of a catheter malfunction.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. A catheter comprising:
    a connector at a proximal side of the catheter for connecting the catheter to an external signal transmission/receiving unit for communicating signals between the catheter and the signal transmission/receiving unit,
    an electrode at a distal side of the catheter configured to be introduced into a patient P, and
    an electrical connection including an electrical wire for electrically connecting the electrode and the connector for the transmission of the signals between the electrode and the connector, wherein the electrical connection has a high electrical resistance of at least 1 kΩ to limit any power deposition in a tissue of the patient
    further comprising a current sensing unit R2 configured to sense the electrical current flowing in the electrical connection at the distal side of the catheter and further configured to transmit a sensing signal indicative of the sensed current to an external current control unit.

2. A catheter as claimed in claim 1, wherein the wire has an electrical resistance of at least 1 kΩ.

3. A catheter as claimed in claim 1, wherein the electrical connection comprises a lumped resistor having a resistance of at least 1 kΩ.

4. A catheter as claimed in claim 1, wherein said electrode is adapted for receiving physiological signals.

5. A catheter as claimed in claim 1, wherein said electrical connection comprises a pair of wires for electrically connecting a pair of electrodes with the connector.

6. A catheter as claimed in claim 1, wherein said current sensing unit comprises a sensing resistor R2 having a small electrical resistance of 1 kΩ for sensing a voltage representing said sensing signal and a pair of sensing wires for transmitting said sensing signal to said external current control unit.

7. A catheter as claimed in claim 1, wherein said wire is substantially made of a metal, a metal alloy, carbon fibers, conductive polymers or other conductive non-magnetic material.

8. A catheter as claimed in claim 1, wherein said wire is made of non-conductive fibers or threads coated with a conductive coating.

9. A catheter as claimed in claim 1, wherein said wire is made of non-conductive fibers or threads filled with a conductive filling or conductive particles.

10. Medical assembly comprising:
    a signal transmission/receiving unit configured to communicate and process signals; and
    a catheter including
        a connector at a proximal side of the catheter connecting the catheter to the signal transmission/receiving unit for communicating the signals between the catheter and the signal transmission/receiving unit,
        an electrode at a distal side of the catheter configured to be introduced into a patient P, and
        an electrical connection including an electrical wire for electrically connecting the electrode and the connector for the transmission of the signals between the electrode and the connector, wherein the electrical connection has a high electrical resistance of at least 1 kΩ to limit any power deposition in a tissue of the patient wherein said catheter further includes a current sensing unit R2; and
    further comprising a current control unit configured to limit the current fed into said catheter,
    wherein said current control unit is adapted for receiving a sensing signal from the current sensing unit R2 configured to sense the electrical current flowing in the electrical connection at the distal side of the catheter, said sensing signal being indicative of the sensed current.

11. Medical assembly as claimed in claim 10, wherein said signal transmission/receiving unit includes an ECG monitoring unit configured to monitor received ECG signals or a pacing unit configured to generate pacing signals.

12. Medical assembly as claimed in claim 10, further comprising an MR imaging apparatus configured to generate MR images of the patient P during a medical intervention.

* * * * *